United States Patent [19]

Damon

[11] Patent Number: 5,275,557
[45] Date of Patent: Jan. 4, 1994

[54] SELF-LOCKING ORTHODONTIC BRACKET

[76] Inventor: Dwight H. Damon, E. 12606 21st, Spokane, Wash. 99216

[21] Appl. No.: 45,529

[22] Filed: Apr. 8, 1993

[51] Int. Cl.$^5$ .................................................. A61C 3/00
[52] U.S. Cl. ....................................... 433/10; 433/13; 433/14
[58] Field of Search ......................... 433/10, 11, 13, 14

[56] References Cited

U.S. PATENT DOCUMENTS

| | | | |
|---|---|---|---|
| 1,280,628 | 10/1918 | Angle | 433/14 |
| 1,821,171 | 9/1931 | Atkinson | 433/14 |
| 2,230,315 | 2/1941 | Winslow | 433/11 |
| 2,671,964 | 3/1954 | Russell et al. | 433/13 |
| 3,091,857 | 6/1963 | Rubin et al. | 433/11 |
| 3,128,552 | 4/1964 | Broussard | 433/13 |
| 3,131,474 | 5/1964 | Johnson | 433/11 |
| 3,497,954 | 3/1970 | Kesling | 433/13 |
| 3,835,539 | 9/1974 | Wallshein | 433/14 |
| 4,015,334 | 4/1977 | Moss | 433/17 |
| 4,023,274 | 11/1977 | Wallshein | 433/11 |
| 4,144,642 | 3/1979 | Wallshein | 433/11 |
| 4,180,912 | 1/1980 | Kesling | 433/13 |
| 4,197,642 | 4/1980 | Wallshein | 433/11 |
| 4,209,906 | 7/1980 | Fujita | 433/11 |
| 4,242,085 | 12/1980 | Wallshein | 433/14 |
| 4,248,588 | 2/1981 | Hanson | 433/11 |
| 4,260,375 | 4/1981 | Wallshein | 433/11 |
| 4,355,975 | 10/1982 | Fujita | 433/11 |
| 4,386,909 | 6/1983 | Hanson | 433/20 |
| 4,419,078 | 12/1983 | Pletcher | 433/11 |
| 4,492,573 | 1/1984 | Hanson | 433/11 |
| 4,561,844 | 12/1985 | Bates | 433/10 |
| 4,583,944 | 4/1986 | Hanson | 433/22 |
| 4,698,017 | 10/1987 | Hanson | 433/11 |
| 4,712,999 | 12/1987 | Rosenberg | 433/11 |
| 4,838,787 | 6/1989 | Lerner | 433/14 |
| 4,850,865 | 7/1989 | Napolitano | 433/8 |
| 4,859,179 | 8/1989 | Kesling | 433/8 |
| 5,018,259 | 5/1991 | Wildman | 433/8 |
| 5,094,614 | 3/1992 | Wildman | 433/14 |
| 5,123,838 | 6/1992 | Cannon | 433/14 |
| 5,154,607 | 10/1992 | Hanson | 433/8 |
| 5,174,753 | 12/1992 | Wool | 433/20 |

Primary Examiner—John J. Wilson
Attorney, Agent, or Firm—Wells, St. John, Roberts, Gregory & Matkin

[57] ABSTRACT

A self-locking orthodontic bracket includes a base for attachment to a tooth or tooth band. Transversely spaced tying lugs are fixed to the base and include opposed extensions for orthodontic attachment purposes. The tying lugs present an anterior or front surface interrupted by a transverse archwire slot. A closure mounted on the bracket includes a movable cover slidably engaging the anterior surface of the bracket. The cover spans the full width of the tying lugs and has a perpendicular width greater than the width of the archwire slot across the anterior surface. The closure is supported on the bracket by a pair of guides that slidably engage opposed side surfaces of the tying lugs for opening and closing the cover. The closure can also be designed to complement the archwire slot structure between the lugs, forming a complete tube encircling the archwire across the full width of the bracket when the cover is in its closed position.

24 Claims, 6 Drawing Sheets

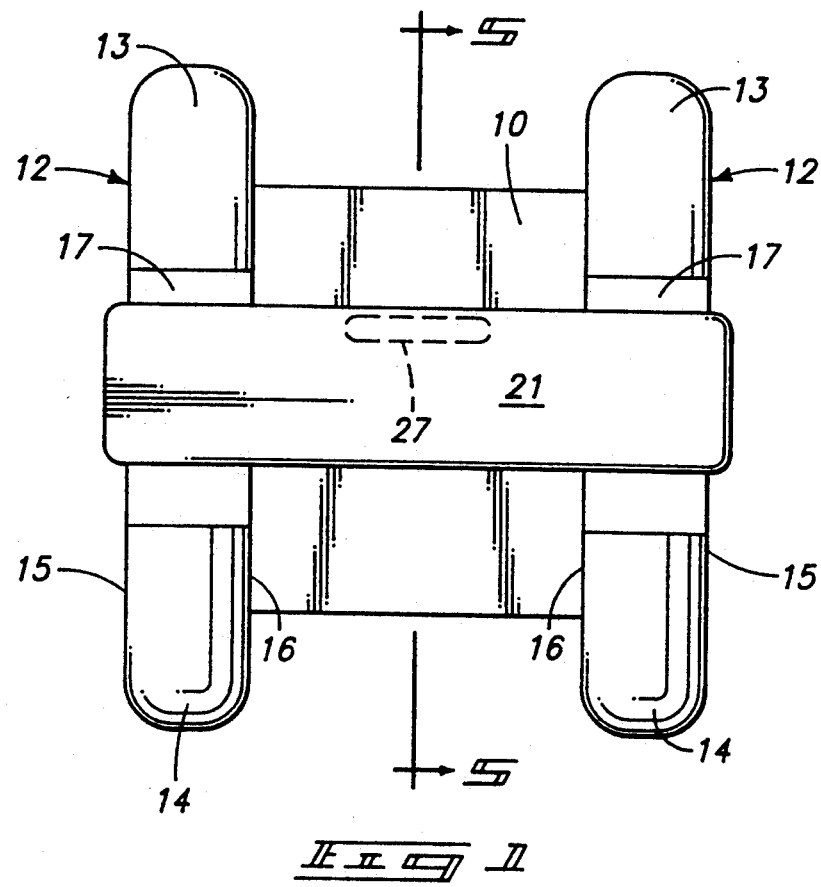
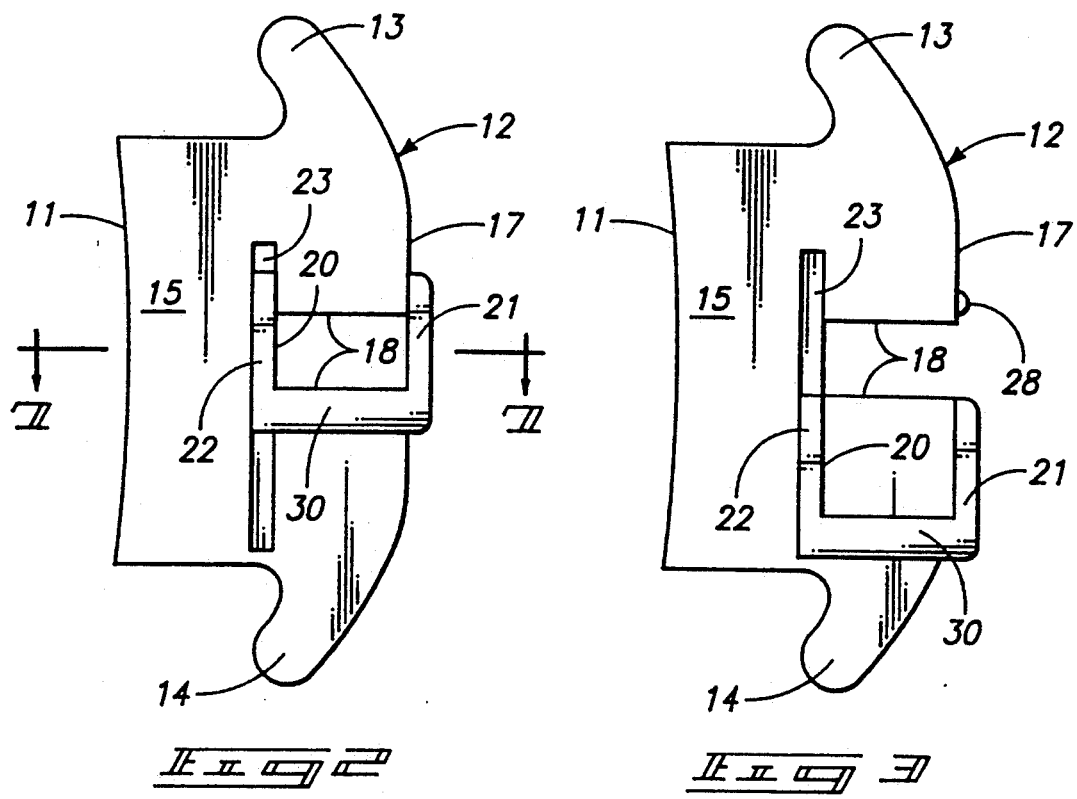

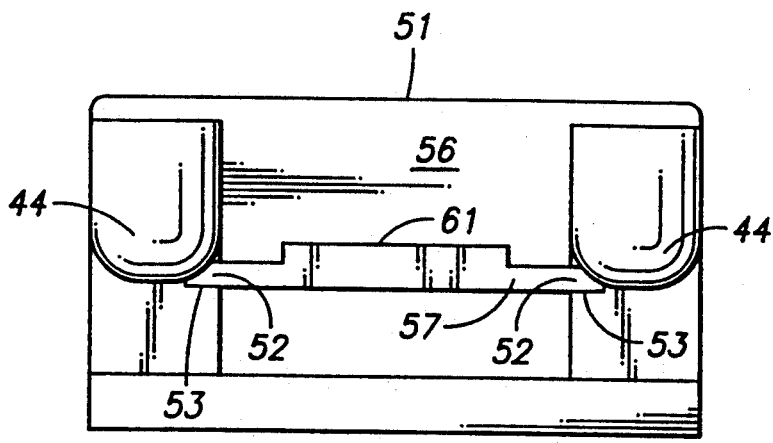
_Fig 12_
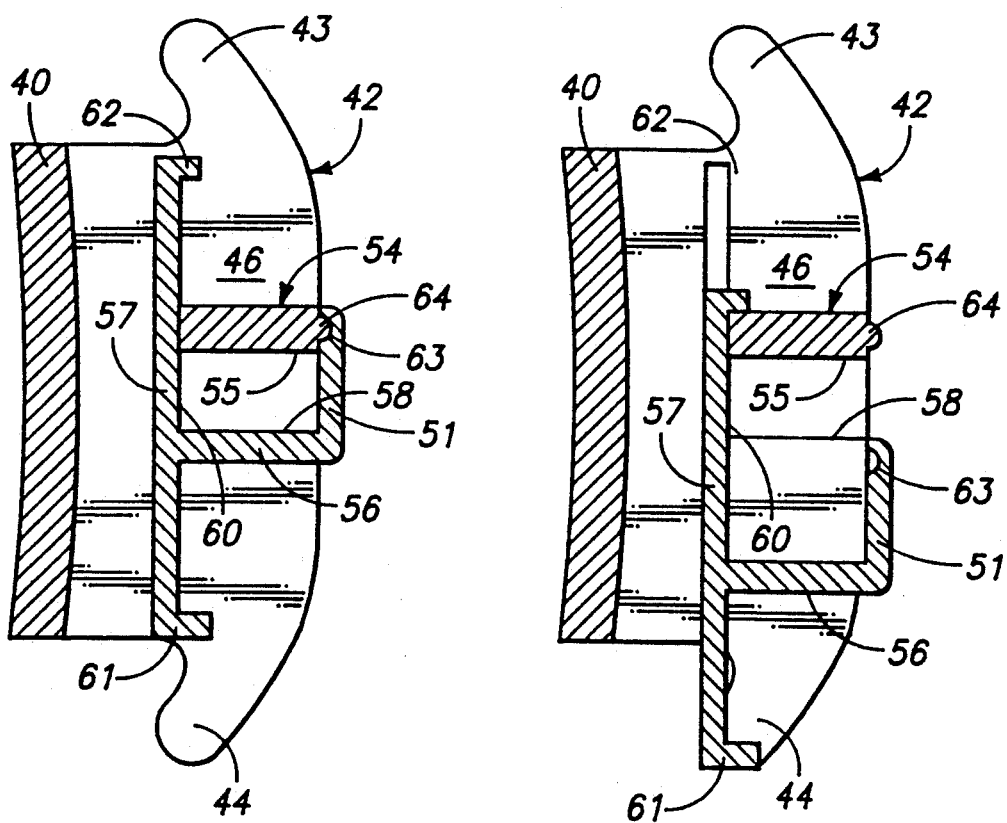
_Fig 13_   _Fig 14_

SELF-LOCKING ORTHODONTIC BRACKET

TECHNICAL FIELD

This disclosure pertains to self-locking or ligatureless orthodontic brackets.

BACKGROUND OF THE INVENTION

Orthodontic brackets attached to teeth are adapted to engage an archwire that exerts forces upon them to move the teeth. Such brackets typically include an archwire slot for reception of the archwire. An archwire slot can have any desired cross-sectional configuration or size to match requirements of the archwire, or archwires, that are to be engaged within the slot.

Orthodontic brackets are typically bonded to a tooth or to a tooth band with the archwire slot oriented parallel to the occlusal plane. However, the slot can also be angularly oriented across the bracket when desired.

Most brackets in use today include extensions that project upwardly and downwardly at the top and bottom of the installed bracket, respectively. These extensions permit the archwire to be held within the archwire slot of the bracket by means of a twisted wire (ligature) or an elastomer O-ring.

Numerous attempts have been made to design brackets that are self-locking or ligatureless. A detailed discussion of patents and publications describing various closures that have been proposed for the archwire slots of such orthodontic brackets can be found in U.S. Pat. No. 5,094,614 to Wildman, issued Mar. 10, 1992, which is hereby incorporated into this disclosure by reference.

As recognized in the Wildman patent, an ideal locking device for an orthodontic bracket should leave the top and bottom of the bracket, including the projections conventionally used for anchoring the tying wires, free to receive other attachments or auxiliary devices.

The Wildman patent discloses a slidable closure that engages the front of the archwire. The closure is recessed from the front or anterior surfaces of the disclosed bracket. This is also true of sliding closures shown in U.S. Pat. No. 2,671,964 to Russell et al., which was issued on Mar. 16, 1954 and in U.S. Pat. No. 3,131,474, which was issued on May 5, 1964 to Johnson. The fact that such recessed sliding closures require the archwire also to be recessed within the archwire slot before the closure can be moved over the archwire makes it very difficult for the user to visually confirm that the archwire is properly seated within the archwire slot to facilitate closing of the slidable cover.

When using a conventional bracket and tying wires, proper seating of the archwire can be confirmed by visually noting that the anterior surface of the archwire is flush with the anterior surface of the bracket. It is desirable that a self-locking bracket provide similar visual reference capabilities to the user. This cannot be attained where a sliding closure is recessed within the bracket.

A flush-mounted closure in the form of a spring clip is shown in various embodiments illustrated within U.S. Pat. No. 4,023,274 to Wallshein, issued on May 17, 1977. In FIGS. 4A and 4B of the Wallshein patent, there is illustrated a spring clip having a closure panel that extends across the full width of a bracket and covers aligned slots in two separate lugs. However, the spring clip also covers the bottom of the bracket and presents a separable bracket element that must be attached to the bracket prior to its utilization. A sliding closure is more easily manipulated than a spring clip. Slidable closures are particularly desirable because they substantially reduce the time required for opening and closing of the archwire slots during periodic adjustment of the archwire and brackets.

The present bracket was designed to mount an archwire flush with the anterior surface of an orthodontic bracket to facilitate visual positioning of the archwire during orthodontic treatment. It also was designed to utilize a sliding closure that is permanently retained on the bracket during use, whether the closure is left in an open or closed condition. This guards against accidental release of the closure while the bracket is worn on a tooth.

Most importantly, the closure has been designed to leave the usual tying extensions that protrude from the top and bottom of the bracket fully accessible to other orthodontic attachments to apply torsional forces to the teeth. The exposed tying lugs remain always available for repositioning of the bracket and tooth by use of tying wires or other conventional attachment systems.

The present bracket also includes a closure that completes a continuous tube surrounding the archwire when the closure is in a closed position. This can be effectively achieved in a Siamese bracket configuration without covering or interfering with projecting extensions on the bracket.

Creation of a continuous tube surrounding the archwire across the full width of the bracket eliminates the binding of the archwire within the confines of the bracket which occurs across the corners typically presented by conventional slotted bracket lugs.

BRIEF DESCRIPTION OF THE DRAWINGS

Preferred embodiments of the invention are described below with reference to the accompanying drawings, which are briefly described below.

FIG. 1 is an elevational view of an assembled bracket with the cover in a closed position;

FIG. 2 is a side view of the bracket;

FIG. 3 is a side view of the bracket with the cover in an open position;

FIG. 12 is a bottom view of the bracket;

FIG. 13 is a sectional view taken along line 13—13 in FIG. 9;

FIG. 14 is a cross-sectional view similar to FIG. 13, showing the closure in an open position;

DETAILED DESCRIPTION OF THE PREFERRED EMBODIMENTS

Figure 4:
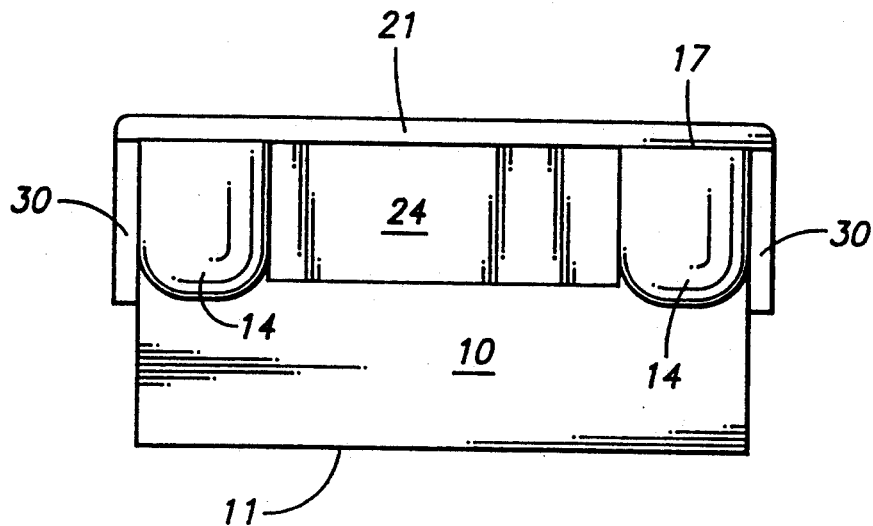
FIG. 4 is a bottom view of the bracket.

This disclosure of the invention is submitted in furtherance of the constitutional purposes of the U.S. Patent Laws "to promote the progress of science and useful arts" (Article 1, Section 8).

Two illustrative forms of the self-locking orthodontic bracket are illustrated in the drawings. A first preferred embodiment is shown in FIGS. 1-8. An alternative embodiment is shown in FIGS. 9-17.

When referring to the illustrated form of bracket, the front surfaces of the bracket, directed outwardly from a supporting tooth, shall be referred to as anterior surfaces. Conversely, the rear surfaces, which face toward the tooth, shall be termed posterior surfaces. Directions along the bracket generally parallel to the incisal or occlusal line shall be referred to as having width and being transverse. Conversely, perpendicular directions extending between the gingival line and the incisal or occlusal line shall be referred to as the height of the bracket. The upright surfaces across the bracket shall be termed its side surfaces and the surfaces along the top and bottom of the bracket shall be termed the incisal or occlusal surface or the gingival surface.

The incisal or occlusal surface and the gingival surface of the bracket are interrupted by projections that form cleats or anchors for tying wires and other attachment devices. The configurations of these extensions can take any desired conventional or unconventional form. The extensions at the top and bottom of the bracket can be located in different planes. The extensions at the top of the bracket can be located in a plane different from that of the extensions at the bottom of the bracket. The extensions might also have the same or a different configuration at the top of the bracket than at the bottom of the bracket.

Similarly, the archwire slot across each bracket can be oriented at any desired angular configuration relative to its incisal or occlusal surface. The archwire slots shown in the illustrative drawings are aligned transversely across each bracket in a direction parallel to the incisal or occlusal surface for general illustration purposes.

The illustrated brackets can be bonded directly to a tooth or can be mounted on a tooth band for attachment to a tooth at either the facial or lingual tooth surfaces.

The present bracket can be made from any suitable material, including metals, plastics and ceramics, as well as a combination of such materials. The bracket and closure have generally been designed to be fabricated of metal, but the choice of materials is not critical to understanding or using this invention. The only limitation with regard to materials is the ability to efficiently fabricate or mold the bracket and closure as a cooperative mechanism to engage an archwire during orthodontic procedures.

The general concepts of the invention can best be understood from a study of the first embodiment of the assembled orthodontic bracket, illustrated in FIGS. 1-7. This form of the bracket includes a movable closure separately shown in FIG. 8.

The illustrated bracket includes a supportive base 10 having a posterior surface 11 adapted to be bonded to a tooth or tooth band.

A pair of tying lugs 12 project anteriorly from base 10. Each lug 12 includes opposed extensions 13 and 14 that project outwardly between transversely spaced side surfaces formed on the bracket. At a minimum, the tying lugs 12 each include an outer side surface 15. In addition, the tying lug configurations shown in the drawings further include inwardly facing side surfaces 16 formed across each tying lug 12.

The bracket also includes an anterior surface 17 across the front of each tying lug 12. The anterior surface 17 is illustrated as being planar, but can be curved if desired. It is interrupted by the opening of a transverse archwire slot formed distally from the anterior surface 17. The archwire slot spans the full width of the bracket, where it opens across the bracket side surfaces 15 (see FIGS. 2, 3 and 7).

The archwire slot includes side slot surfaces 18 and an anterior slot surface 20. The slot surfaces 18 and 20 are sized and configured in a manner complementary to the size and shape requirements of an archwire (or archwires) adapted to be received within the archwire slot. While the illustrated slot is rectangular and is designed specifically for reception of a complementary rectangular archwire, it is to be understood that the slot can be configured as a cylinder or other cross-sectional shape in the manner presently known with respect to orthodontic bracket design. In use, the slot is partially or completely filled by the cross-sectional configuration of one or more archwires located within it.

A closure complementary to the archwire slot is also provided on the illustrated bracket. It includes a movable cover 21 that slidably engages the anterior surface 17. Cover 21 has a width that spans the full width of the tying lugs 12 between their respective side surfaces 15. Its perpendicular width is greater than the corresponding width across the archwire slot at the anterior surface 17 of the bracket.

Figures 5, 6:
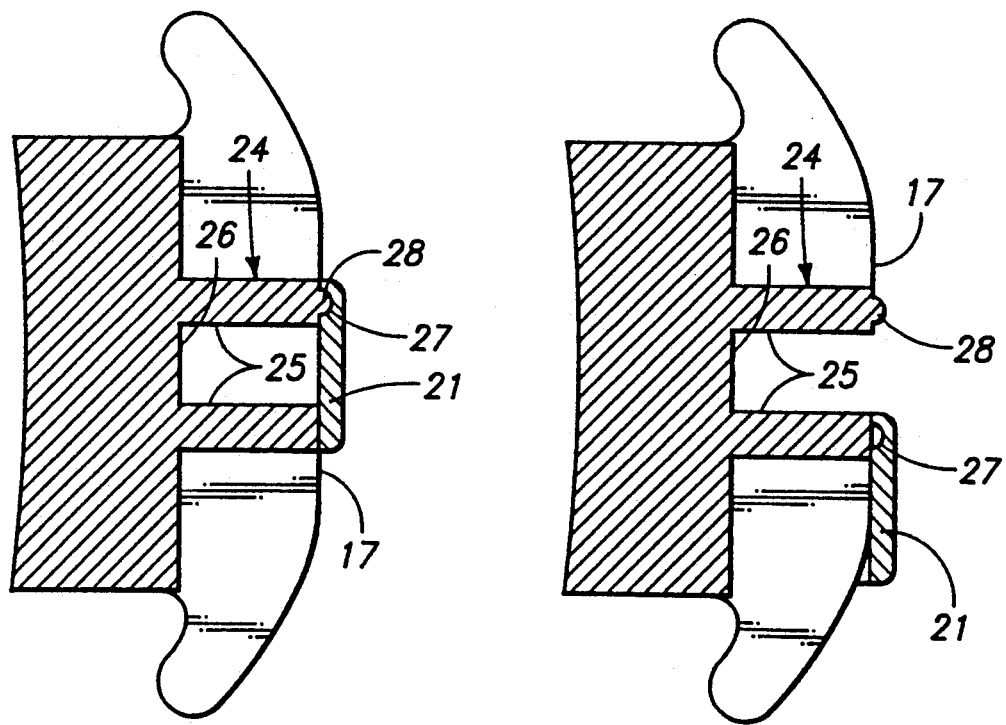
FIG. 5 is a sectional view as seen along line 5—5 in FIG. 1.
FIG. 6 is a sectional view similar to FIG. 5, showing the cover in an open position.

The closure further includes a pair of guides 22 spaced transversely apart from one another along the width of the bracket. The guides slidably engage opposed side surfaces 15 within complementary grooves 23. Movement of the cover and guides relative to the tying lugs 12 alternately positions the closure in (1) a first position with the cover clear of the archwire slot (FIGS. 2, 5) or (2) a second position with the cover 21 overlapping the width and height of the archwire slot (FIGS. 3, 6).

The above description includes only those elements basic to Siamese brackets, which include transversely spaced tying lugs protruding from a supporting base. However, additional strength and the benefits of an enclosed archwire tube can be imparted to this bracket by also providing a fixed transverse wall extending between the inner side surfaces 16 of the respective tying lugs 12. This wall, shown at 24, structurally interconnects the tying lugs 12 and base 10.

Wall 24 includes inner surfaces 25 aligned with the side slot surfaces 18 in the respective tying lugs 12. Either the wall 24 or base 10 also presents a perpendicular transverse surface 26 aligned with the anterior slot surfaces 20 along the respective tying lugs 12. The resulting open slot along the bracket is formed continuously from one side of it to the other, thereby eliminating the sharp edged corners that would otherwise be presented at the inner side surfaces 16 of the tying lugs 12.

Wall 24 is illustrated as a rather narrow structure spanning the two sides of the transverse archwire slot. However, it is to be understood that the thickness of wall 24 can be expanded to encompass the full height of the bracket across the illustrated base 10, while still leaving extensions 13 and 14 protruding openly at the top and bottom of the bracket.

Figure 7:
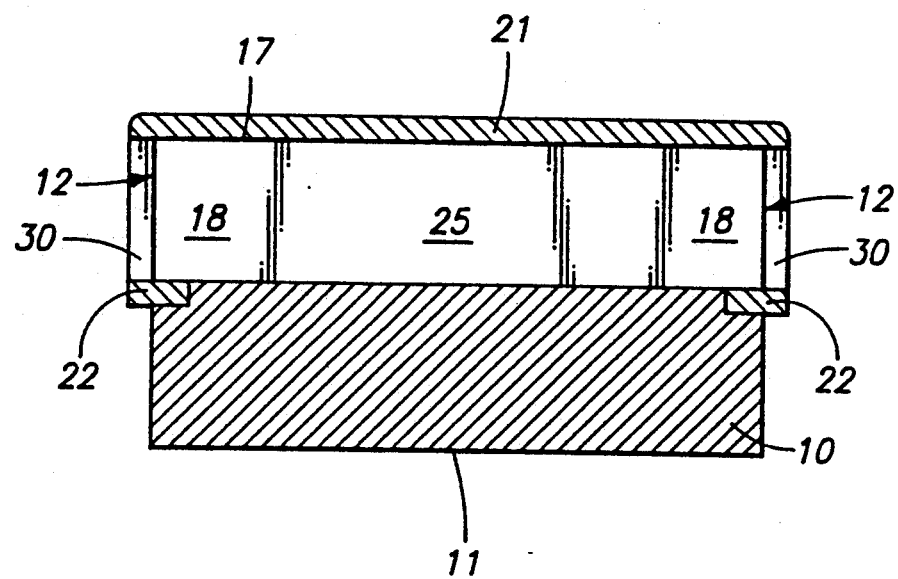
FIG. 7 is a sectional view taken along line 7—7 in FIG. 2.
Figure 8:
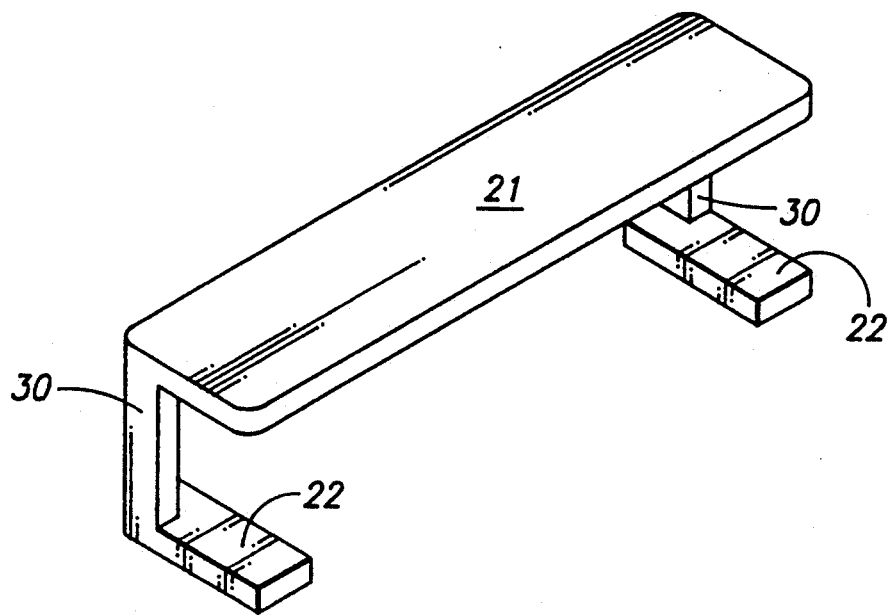
FIG. 8 is a perspective view of the closure shown in FIGS. 1-7.
Figure 9:
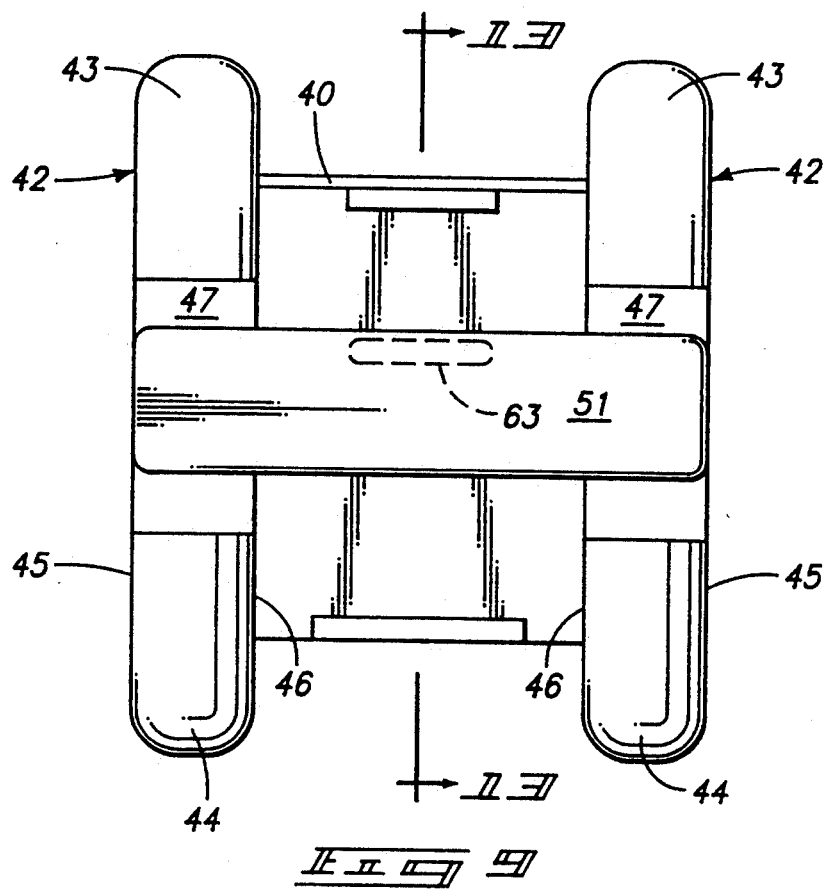
FIG. 9 is an elevational view of a second embodiment of the bracket.
Figures 10, 11:
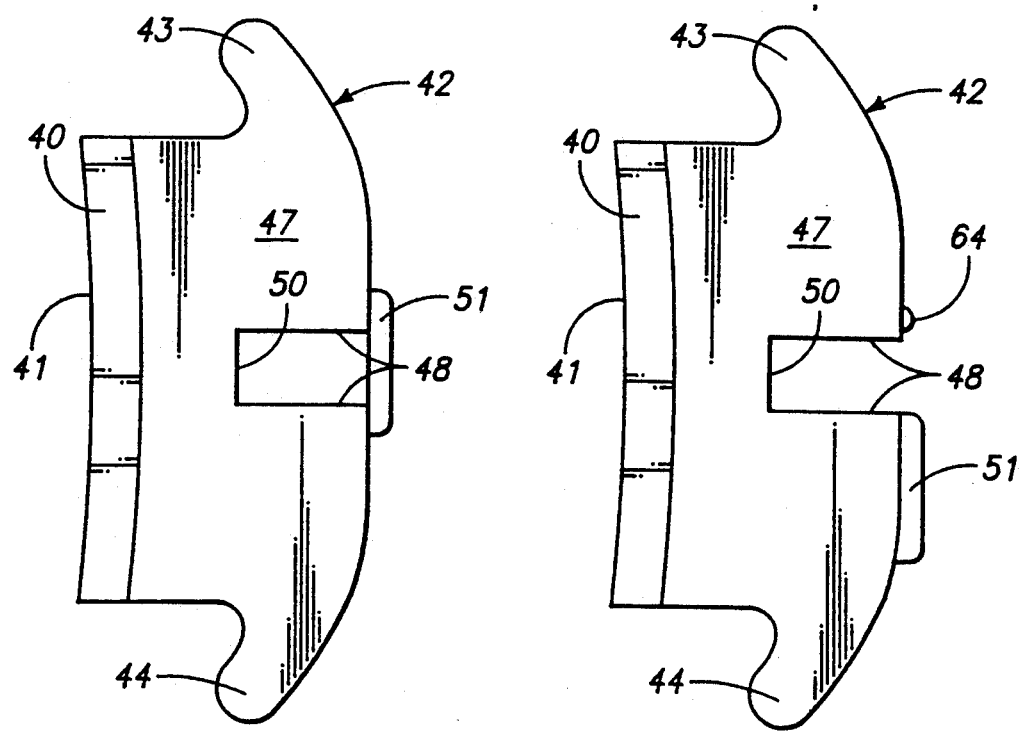
FIG. 10 is a side view of the bracket shown in FIG. 9.
FIG. 11 is a side view showing the closure in an open position.

As can be seen in FIG. 7, the side slot surfaces 18 along the tying lugs 12 and the inwardly facing surfaces 25 within transverse wall 24 merge to form continuous inner slot surfaces extending across the full width of the bracket. They intersect similarly merging anterior slot surfaces 20 and 26, as previously described. When enclosed by cover 21, as shown in FIGS. 2 and 5, these surfaces and the movable cover form a fully enclosed tube for engagement of an archwire across the complete width of the bracket.

Cover 21 and guides 22 are structurally interconnected by an interposed pair of rigid support members shown at 30. The support members 30, together with cover 21 and guides 22 form a separable closure generally illustrated in FIG. 8. This closure can be molded or fabricated independently from the bracket. It should be assembled on the bracket prior to installation of the bracket on a tooth ot tooth band. While the closure is normally retained on the bracket during its use, it can be forced free from the bracket for replacement purposes or when use of the closure is not required. The design of the bracket and closure should be such that removal of the closure can only be achieved by substantial prying movement, such as might be applied through use of a scaler.

It is preferable that cover 21 be releasably locked in its closed position to ensure against accidental release of an archwire received within the archwire slot. Releasable detents or locks can be provided between the cover 21 and the bracket or between the guides 22 and the bracket. As an illustrative locking device, the open edge of cover 21 has an inwardly recessed groove 27 formed along its transverse center. The groove 27 releasably engages a complementary ridge 28 formed along the transverse center of the overlapped anterior surface of transverse wall 24. While generally rigid, the cover 21 must then have sufficient flexibility to yield slightly to ride over the ridge 28 as the cover 21 is moved between its operative positions.

It is also desirable that cover 21 not be accidentally released from engagement with the supporting bracket structure while within the mouth of a patient. This can be achieved by provision of positive stops on the guides 22 to limit their extent of sliding movement along the receiving grooves 23. Removal of cover 21 might also be prevented by protrusions (not shown) that extend outwardly from side surfaces 15 in the path of the rigid support members 30 that interconnect cover 21 and guides 22. In the embodiment illustrated, outward movement of cover 21 is limited by the extent of groove 27, which terminates short of the adjacent side edge along the bracket. The design and operation of these detents, locks and motion limiting features is subject to many variations and are not essential to an understanding of the present invention.

The bracket and closure are preferably mounted on a tooth with the open edge of the closure facing toward the gingival line. Thus, biting pressures on food will tend to maintain the closure in a closed condition over the archwire received in the archwire slot.

The support members 30 are respectively located adjacent to the side surfaces 15 across the tying lugs 12. Each support member 30 leads posteriorly from the cover 21 to one of the guides 22.

The sliding guides 22 are illustrated as being parallel to the portions of the anterior surface 17 slidably engaged by cover 21. Thus, the movement imparted to the supported cover 21 will maintain it in a parallel position with its inner surface flush against the overlapped areas of anterior surface 17. This will maintain cover 21 in a closely adjacent position to the stationary bracket structure regardless of whether cover 21 is in its open or closed positions. If the anterior surface 17 is transversely curved, the guides 22 and grooves 23 might be similarly curved to achieve the desired flush sliding relationship between surface 17 and cover 21.

When in its open position, as shown in FIGS. 3 and 6, cover 21 will leave the slot clear for movement of an archwire into or out from the slot. In addition, the protruding extensions 13 at all times remain clear and accessible for tying or attachment purposes.

Guides 22 are located on the bracket in positions that are posterior to the open slot formed transversely through it. As can be seen in FIGS. 2 and 3, the support members 30 are offset from the center line of the closure to assure that there is adequate clearance across the full width of the archwire slot when the cover 21 is in its closed position. Thus, transverse sliding movement of the guides 22 and support members 30 does not block or restrict access to any portion of the open transverse archwire slot.

FIGS. 9-17 illustrate a second form of the invention in which the transverse separation of the tying lugs across the supportive base is more pronounced. The elements of the bracket and cover common to those previously disclosed herein will not be described again in repetitious detail.

The second embodiment of the improved bracket also includes a mounting base 40 having a posterior surface 41. A pair of transversely spaced tying lugs 42 project anteriorly from base 40. They include extensions 43 and 44, which project from the bracket between outer and inner side surfaces 45 and 46 across the tying lugs 42.

An anterior surface 47 is presented along the front of the bracket across the respective tying lugs 42. An archwire slot extends transversely through each tying lug 42. It includes side slot surfaces 48 and a anterior slot surface 50.

The closure as shown in FIGS. 9-17 includes a movable cover 51 supported by a pair of guides 52. The guides 52 are slidably engaged within complementary grooves 53 formed across the inner side surfaces 46 of the respective tying lugs 42. Grooves 53 and guides 52 are located posteriorly with respect to the anterior slot surface 50 of the archwire slot.

A transverse wall 54 spans the two tying lugs 42. It is preferably molded integrally with the tying lugs 42 and base 40. An inner surface 55 along wall 54 is aligned with one side slot surface 48 as an integral extension of it, thereby forming a continuous side slot surface extending the full width of the illustrated bracket.

The closure of the second embodiment, like that of the first, has a structure that is complementary to the archwire slot. Since the inner surface 55 of transverse wall 54 is coextensive and flush with at least a portion of the inner archwire slot surfaces, namely one side slot surface 48, the remaining surfaces required to complete the archwire slot in the space between tying lugs 42 must be supplied by the movable closure. As shown, these surfaces are provided on support members 56 and 57 that structurally interconnect cover 51 to guides 52.

In the illustrated embodiment, structural member 56 is perpendicular to the attached cover 51. It has an inner surface 58 aligned with the remaining side slot surface 48 along the archwire slot. Structural member 57 is a shelf arranged in a position that is parallel to cover 51. Guides 52 are formed as outward extensions along its opposed sides. An inner surface 60 along structural member 57 is aligned with the anterior slot surface 50 of the archwire slot when the cover 51 is in its closed position.

Structural member 57 is also provided with an upturned side 61 that can serve as a manual handle or grip to facilitate opening or closing of cover 51 relative to the supporting orthodontic bracket. The opposite side of structural member 57 is shown with an upturned central section 62 that can serve as a stop capable of abutting transverse wall 54 and limiting the extent of opening movement that can be imparted to cover 51.

An inwardly facing central groove 63 adjacent to the free edge of cover 51 and a complementary ridge 64 across the top central section of transverse wall 54 are illustrative of a detent or lock for maintaining cover 51 in its closed position overlapping the archwire slot.

The above two embodiments are intended to merely illustrate the basic structural features of the improved orthodontic bracket. In both, the closure that completes the archwire slot comprises a slidable mechanism supported on the bracket at a location that is behind or posterior to the archwire slot boundaries. Sliding support for the closure can be provided either along inwardly facing side surfaces or outwardly facing side surfaces of the bracket. In both arrangements, the closure is movable between a first position clear of the archwire slot and a second position overlapping the its width and height.

When used in conjunction with a bracket design that further includes at least a portion of the slot structure between spaced tying lugs, the closure can also supply complementary surfaces movable between the lugs to fully complete a continuous archwire tube across the full width of the bracket.

Figure 15:
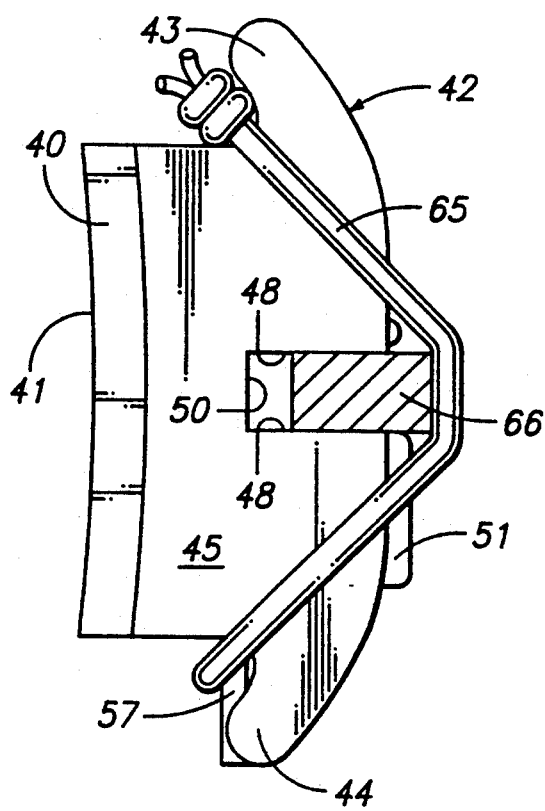
FIG. 15 is a side view of the bracket, illustrating use of a tying wire to retain the bracket on an archwire.
Figures 16, 17:
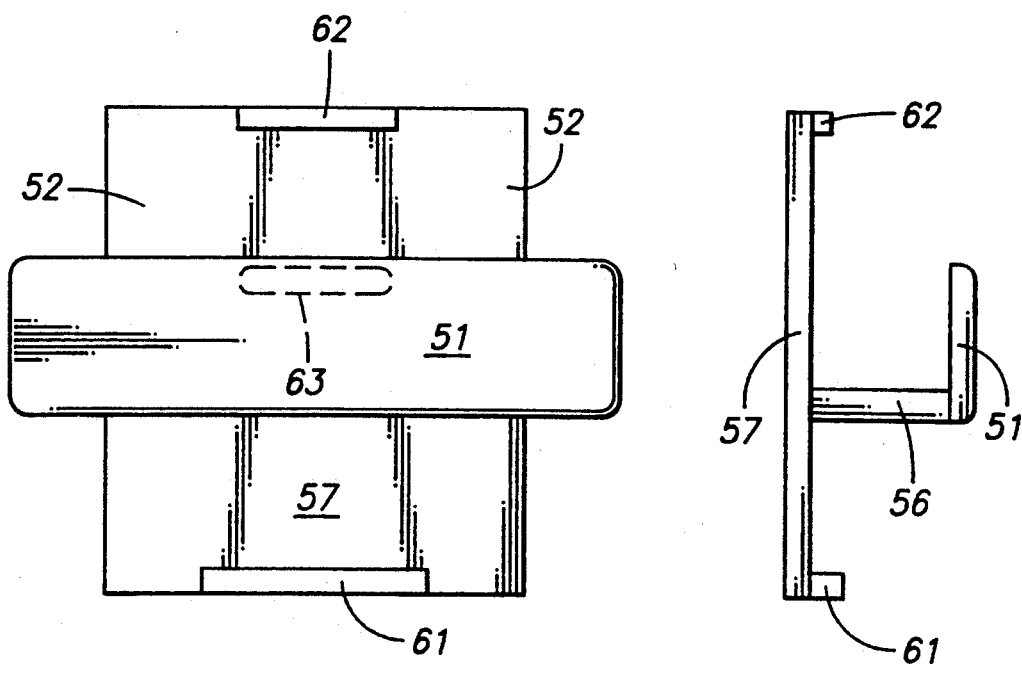
FIG. 16 is an elevational view of the closure.
FIG. 17 is a side view of the closure.

In both embodiments, the closure does not impede normal access to and use of the tying lugs. The extensions that protrude to the sides of the orthodontic bracket remain unobstructed at all times. The bracket can therefore be used to apply torsional forces to a tooth to rotate it about a desired axis or to use ligatures to interconnect the bracket and archwire where this is required. As an example, FIG. 15 illustrates the use of a tie wire 65 wrapped about extensions 43 of the second illustrated embodiment of the invention.

A conventional tie wire 65 might be used to secure the bracket to an archwire 66 when the current position of the attached tooth is such that the archwire 66 cannot be completely positioned within the archwire slot of the bracket at a particular stage during orthodontic treatment. By leaving the closure open and using tie wires 65 to move the tooth relative to the archwire 66, a practitioner can utilize the present bracket at treatment stages prior to that at which use of the self-locking feature of the bracket becomes practical. Similarly, tying wires, bands and other devices can be attached to the extensions of the bracket at any time to apply rotative forces or attach other orthodontic devices to the bracket.

In the preferable forms of the invention, where the closure completes a continuous tube that can surround an archwire along the full width of the bracket, the tube structure eliminates the corners conventionally encountered along the slotted lugs on dual or Siamese orthodontic brackets. These corners typically exert binding forces on the archwire, which impede tooth movement by the resulting concentration of frictional forces along the width of the archwire. The continuous tube formed by the preferred forms of this invention assures freedom of movement of the bracket relative to the archwire, thereby increasing the rate of tooth movement and reducing the need for frequent manual readjustment of the brackets during treatment.

Another very important result of the present invention is the fact that the archwire, when properly received within the archwire slot of the bracket, is at least flush with the outer or anterior surface of the bracket. Proper reception of the archwire within the receiving archwire slot and the ability to close the cover over the archwire can therefore be readily confirmed by visual inspection of the bracket within the mouth. This is contrasted with the difficulty of gauging the archwire positions within earlier brackets having slidable closures recessed beneath the anterior surface.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A self-locking orthodontic bracket, comprising:
   a base having a posterior surface adapted to be bonded to a tooth or tooth band;
   tying lug means mounted to the base and projecting anteriorly from it, the tying lug means including opposed extensions that project outwardly between transversely spaced side surfaces formed on the bracket;
   the tying lug means further including an anterior surface interrupted by a flush opening leading to a transverse archwire slot formed distally from the anterior surface and spanning the full width of the tying lug means, the archwire slot having inner slot surfaces configured complementary to the size and shape of an archwire adapted to be received within the archwire slot; and
   a closure including a movable cover slidably engaging the anterior surface of the tying lug means, the closure having a width that spans the full width of the tying lug means and a perpendicular height that is greater than the corresponding height of the opening of the archwire slot across the anterior surface;
   the closure further including a pair of guides transversely spaced from one another across the bracket, the guides slidably engaging opposed side surfaces of the tying lug means for alternately positioning the closure means in (1) a first position with the cover clear of the archwire slot or (2) a second position with the cover overlapping the width and height of the opening of the archwire slot.

2. The self-locking orthodontic bracket of claim 1, wherein the guides are located posteriorly of the archwire slot.

3. The self-locking orthodontic bracket of claim 1, wherein the guides are parallel to the portions of the anterior surface slidably engaged by the cover.

4. The self-locking orthodontic bracket of claim 1, wherein the closure further includes support members interconnecting the cover and the guides.

5. The self-locking orthodontic bracket of claim 1, wherein the closure further includes support members interconnecting the cover and the guides, the support members having inner surfaces that complement the archwire slot to complete a continuous archwire tube that extends along the full width of the tying lug means when the cover is in its second position.

6. A self-locking orthodontic bracket, comprising:
 a base having a posterior surface adapted to be bonded to a tooth or tooth band;
 a pair of tying lugs mounted to the base and projecting anteriorly from it in transversely spaced parallel positions, the tying lugs each including at least one side surface transversely spaced from one another and opposed extensions that project outwardly between their respective side surfaces;
 the tying lugs further including an anterior surface interrupted by flush openings leading to transverse archwire slots formed distally from the anterior surface along the respective tying lugs, the archwire slots having aligned inner slot surface areas configured complementary to the size and shape of an archwire adapted to be received within them;
 a movable cover slidably engaging the anterior surface of the tying lugs, the cover having a width that spans the full width of the pair of tying lugs and a perpendicular height that is greater than the height of the openings of the archwire slots across the anterior surface; and
 a pair of guides operably supporting the cover and slidably engaging oppositely facing side surfaces on the respective tying lugs for alternatively positioning the cover in (1) a first position clear of the archwire slots or (2) a second position overlapping the width and height of the openings of the archwire slots.

7. The self-locking orthodontic bracket of claim 6, wherein the guides engage side surfaces of the respective tying lugs which face inwardly toward one another.

8. The self-locking orthodontic bracket of claim 6, wherein the guides engage side surfaces of the respective tying lugs which face outwardly from one another.

9. The self-locking orthodontic bracket of claim 6, wherein the guides are located posteriorly of the archwire slots.

10. The self-locking orthodontic bracket of claim 6, further comprising:
 a fixed wall extending between the tying lugs, the fixed wall having a surface coextensive and flush with at least a portion of the inner archwire slot surface areas.

11. The self-locking orthodontic bracket of claim 6, wherein the inner slot surface areas of the archwire slot include intersecting slot surfaces aligned across the respective tying lugs, the bracket further comprising:
 a fixed wall extending along the space separating the tying lugs, the fixed wall having inner surfaces coextensive and flush with at least one of the inner slot surfaces.

12. The self-locking orthodontic bracket of claim 6, wherein the inner slot surface areas of the archwire slot include intersecting inner slot surfaces aligned across the respective tying lugs, the bracket further comprising:
 a fixed wall extending along the space separating the tying lugs, the fixed wall having intersecting inner surfaces coextensive and flush with the inner slot surfaces to extend the archwire slots continuously across the width of the bracket.

13. The self-locking orthodontic bracket of claim 6, further comprising:
 a pair of support members structurally interconnecting the cover and the pair of guides, the pair of support members being respectively located adjacent corresponding side surfaces of the tying lugs with each support member leading posteriorly from the cover to one of the guides.

14. The self-locking orthodontic bracket of claim 6, wherein the inner slot surface areas of the archwire slot include intersecting inner slot surfaces aligned across the respective tying lugs, the bracket further comprising:
 a fixed wall extending along the space separating the tying lugs, the fixed wall having an inner surface coextensive and flush with one of the inner slot surfaces along the respective lugs to extend the one inner slot surface continuously along the width of the bracket.

15. The self-locking orthodontic bracket of claim 6, wherein the inner slot surface areas of the archwire slot include intersecting inner slot surfaces aligned across the respective tying lugs, the bracket further comprising:
 a fixed wall extending along the space separating the tying lugs, the fixed wall having an inner surface coextensive and flush with one of the inner slot surfaces along the respective lugs to extend the one inner slot surface continuously across the width of the bracket;
 the fixed wall being interconnected to the tying lugs and the base of the bracket.

16. The self-locking orthodontic bracket of claim 6, wherein the inner slot surface areas of the archwire slot include intersecting slot surfaces aligned across the respective tying lugs, the bracket further comprising:
 a fixed wall extending along the space separating the tying lugs, the fixed wall having an inner surface area that is coextensive and flush with at least one of the slot surfaces; and
 a support member spanning the space between the pair of tying lugs and structurally interconnecting the cover and guides, the support member including at least one inner surface area that complements the inner surface area of the fixed wall to complete a continuous archwire tube when the closure is in its second position.

17. The self-locking orthodontic bracket of claim 6 further comprising:
 a support member spanning the space between the pair of tying lugs and structurally interconnecting the cover and guides, the support member including an inner surface coextensive and flush with at least a portion of the inner slot surface areas of the archwire slots when the closure is in its second position.

18. The self-locking orthodontic bracket of claim 6, further comprising:
 a support member spanning the space between the pair of tying lugs and structurally interconnecting the cover and guides, the support member including at least one inner surface coextensive and flush with a corresponding inner slot surface area of the archwire slots when the closure is in its second position.

19. A self-locking orthodontic bracket, comprising:
a base having a posterior surface adapted to be bonded to a tooth or tooth band;
a pair of tying lugs mounted to the base and projecting anteriorly from it in transversely spaced parallel positions, the tying lugs each including at least one side surface transversely spaced from one another and opposed extensions that project outwardly between their respective side surfaces;
the bracket further including an anterior surface interrupted by a transverse archwire slot leading distally from it across its full width, the archwire slot having inner slot surfaces that open through the side surfaces of the tying lugs and are configured complementary to the size and shape of an archwire adapted to be received within the archwire slot;
a movable cover slidably engaging and flush with the anterior surface of the bracket, the cover overlapping the full transverse width of the pair of tying lugs and having a perpendicular width that is greater than the width of the archwire slot across the anterior surface;
a pair of guides operably supporting the cover and slidably engaging the side surfaces on the respective tying lugs at a location posterior to the archwire slots for alternatively positioning the cover in (1) a first position clear of the archwire slots with the archwire slots opened or (2) a second position overlapping the archwire slots; and
a pair of support members structurally interconnecting the cover and the pair of guides, the pair of support members being respectively located adjacent the side surfaces of the tying lugs with each support member leading posteriorly from the cover to one of the guides.

20. The self-locking orthodontic bracket of claim 19, further comprising:
a transverse wall integrally joining the pair of tying lugs, the archwire slot being formed continuously across the transverse wall and tying lugs throughout the width of the bracket; and
the cover, when in its second position, completing a continuous archwire tube extending across the full width of the bracket and adapted to encircle one or more archwires.

21. The self-locking orthodontic bracket of claim 19, further comprising:
a transverse wall including an extension of the anterior surface and integrally joining the pair of tying lugs and the base, the archwire slot being formed continuously along an opening formed in the transverse wall and tying lugs throughout the width of the bracket; and
the cover, when in its second position, completing a continuous archwire tube extending across the full width of the bracket.

22. A self-locking orthodontic bracket, comprising:
a base having a posterior surface adapted to be bonded to a tooth or tooth band;
a pair of tying lugs mounted to the base and projecting anteriorly from it in transversely spaced parallel positions, the tying lugs each including first and second side surfaces transversely spaced from one another along the bracket and opposed extensions that project outwardly from the lugs;
the bracket further having an anterior surface interrupted by the opening of a transverse archwire slot leading distally from the anterior surface, the archwire slot having an inner slot surface area intersecting the side surfaces of the tying lugs and configured complementary to the size and shape of an archwire adapted to be received within them;
a transverse wall formed distally from the anterior surface and extending between the first side surfaces of the respective lugs, the transverse wall having at least one inner surface formed as a continuation of at least a portion of the transverse archwire slot;
a movable cover slidably engaging and flush with the anterior surface of the bracket, the cover overlapping the full transverse width of the pair of tying lugs and having a perpendicular width that is greater than the width of the archwire slot across the anterior surface;
a pair of guides operably supporting the cover and slidably engaging the side surfaces on the respective tying lugs at a location posterior to the archwire slots for alternatively positioning the cover in (1) a first position clear of the archwire slots with the archwire slots opened or (2) a second position overlapping the archwire slots;
support members structurally interconnecting the cover and the pair of guides, the support members spanning the transverse separation between the two tying lugs and being configured with at least one inner surface shaped to complete a continuous archwire tube that extends across the full width of the bracket when the cover is in its second position.

23. The self-locking orthodontic bracket of claim 22 wherein the archwire slot has a rectangular cross-sectional shape formed by intersecting planar side and anterior slot surfaces along the respective tying lugs and wherein the surface of the transverse wall formed as a continuation of at least a portion of the transverse archwire slot is aligned with one of the side slot surfaces of each archwire slot;
the inner surfaces of the support members being aligned with the remaining side slot surface and the anterior slot surface of each archwire slot when the cover is in its second position.

24. The self-locking orthodontic bracket of claim 22 wherein the archwire slot has a rectangular cross-sectional shape formed by intersecting planar side and anterior slot surfaces along the respective tying lugs and wherein the surface of the transverse wall formed as a continuation of at least a portion of the transverse archwire slot is aligned with one of the side slot surfaces of each archwire slot;
the support members being two perpendicular elements having intersecting inner surfaces aligned with the remaining side slot surface and the anterior slot surface of each archwire slot when the cover is in its second position.

* * * * *